US010172741B1

(12) United States Patent
Hsieh et al.

(10) Patent No.: US 10,172,741 B1
(45) Date of Patent: Jan. 8, 2019

(54) POWER SAVING WELDING HELMET

(71) Applicant: ARCMASK OPTECH CO., LTD, Taoyuan (TW)

(72) Inventors: Chien-Hsing Hsieh, Taoyuan (TW); Edward Martin, Tanuton, MA (US); Chia-Hung Chen, Taoyuan (TW); Jim Watkins, Tanuton, MA (US)

(73) Assignee: ARCMASK OPTECH CO., LTD, Taoyuan (TW)

( * ) Notice: Subject to any disclaimer, the term of this patent is extended or adjusted under 35 U.S.C. 154(b) by 88 days.

(21) Appl. No.: 15/628,534

(22) Filed: Jun. 20, 2017

(51) Int. Cl.
| | |
|---|---|
| *A61F 9/00* | (2006.01) |
| *A61F 9/06* | (2006.01) |
| *A61F 2/14* | (2006.01) |
| *G01J 1/02* | (2006.01) |
| *G01J 1/04* | (2006.01) |
| *G01J 1/18* | (2006.01) |
| *G02F 1/133* | (2006.01) |

(52) U.S. Cl.
CPC ............... *A61F 9/067* (2013.01); *A61F 2/14* (2013.01); *G01J 1/02* (2013.01); *G01J 1/04* (2013.01); *G01J 1/18* (2013.01); *G02F 1/133* (2013.01); *A61F 9/00* (2013.01); *G01J 2001/0276* (2013.01)

(58) Field of Classification Search
CPC .... A61F 9/067; A61F 2/14; A61F 9/00; G02F 1/133; G01J 1/04; G01J 1/02; G01J 1/18; G01J 2001/0276

USPC ......................................................... 250/205
See application file for complete search history.

(56) References Cited

U.S. PATENT DOCUMENTS

| | | | |
|---|---|---|---|
| 6,552,316 B1 | 4/2003 | Bae | |
| 8,990,964 B2 * | 3/2015 | Anderson | A61F 9/06 2/8.2 |
| 9,922,460 B2 * | 3/2018 | Denis | B23K 9/322 |
| 2012/0176659 A1 | 7/2012 | Hsieh et al. | |

FOREIGN PATENT DOCUMENTS

| | | |
|---|---|---|
| EP | 2191800 A1 | 6/2010 |
| WO | 2005/092263 A1 | 10/2015 |

* cited by examiner

*Primary Examiner* — Seung C Sohn
(74) *Attorney, Agent, or Firm* — Pai Patent & Trademark Law Firm; Chao-Chang David Pai

(57) ABSTRACT

A power saving welding helmet includes a helmet shell and a lens device. The helmet shell includes a mounting hole to contain the lens device. The lens device has an inner surface and an outer surface, and includes a magnetic sensor, a filter control unit, and a filter lens. The control logic module controls the filter lens according to magnetic signals generated by the magnetic sensor. The filter lens includes a first LCD panel and a second LCD panel respectively controlled by different control signals. Therefore, a refresh time of the first LCD panel and a refresh time of the second LCD panel do not synchronize. A welder does not feel the first LCD panel or the second LCD panel flashing, and the welding experiences this as consistent darkness.

12 Claims, 10 Drawing Sheets

POWER SAVING WELDING HELMET

BACKGROUND OF THE INVENTION

1. Field of the Invention

The present invention relates to a welding helmet, and particularly to a welding helmet having a function of automatically adjusting light transmittance.

2. Description of the Related Art

A welder may wear a welding helmet when working. The welding helmet may protect the eyes, face, and neck of the welder from flash burn, ultraviolet light, sparks, infrared light, and heat.

A conventional welding helmet may have a dark lens, and the welder may clearly see a welding position through the dark lens. However, when the welder is not working, the welder may not clearly see the surroundings through the dark lens. Hence, the welder may take off the welding helmet from a position in front of the eyes to clearly see the surroundings.

Another conventional welding helmet may have a function of automatically adjusting light transmittance. The welding helmet may automatically change light transmittance of a viewing lens. Therefore, when a welder is not working, the welder does not have to take off the welding helmet and may still clearly see the surroundings through the viewing lens with higher light transmittance.

However, since the viewing lens is controlled by alternating current (AC) signals and a voltage level of the AC signals may be changed with time, the viewing lens may flash when the voltage level of the alternation current signals is changed. An occurrence frequency of flashes of the viewing lens may correspond to a frequency of the AC signals. Therefore, the frequency of the AC signals may be higher enough to cause persistence of vision. When the frequency of the AC signals is higher, power consumption of the conventional viewing lens may be greater. Therefore, battery of the conventional viewing lens may need to be replaced frequently. Thereby, it is making the welding helmet inconvenient and costly to the welder to use the welding helmet.

SUMMARY OF THE INVENTION

An objective of the present invention is to provide a power saving welding helmet. The power saving welding helmet may reduce power consumption to save more electric power.

To achieve the foregoing objective, the power saving welding helmet includes a helmet shell and a lens device. The helmet shell includes a mounting hole. The lens device is mounted in the mounting hole of the helmet shell.

The lens device has an inner surface and an outer surface, and includes a magnetic sensor, a filter control unit, and a filter lens.

The filter control unit is electrically connected to the magnetic sensor, and the filter lens. The magnetic sensor is mounted on the outer surface of the lens device, and generates and transmits magnetic signals to the filter control unit.

The filter control unit includes a battery, a control logic module, and a phase shift module. The battery is electrically connected to and supplies the electric power to the control logic module, and the magnetic sensor.

The control logic module receives the magnetic signals, and determines whether to generate and output control signals according to the magnetic signals.

The filter lens is a viewing lens. The filter lens includes a first liquid crystal display (LCD) panel and a second LCD panel. The first LCD panel is electrically connected to the control logic module through the phase shift module to receive the control signals shifted by the phase shift module. The second LCD panel is directly electrically connected to the control logic module to receive the control signals generated by the control logic module. The first LCD panel and the second LCD panel are stacked with each other.

When the first LCD panel receives the AC control signals shifted by the phase shift module, the light transmittance of the first LCD panel may be lowered, such that the first LCD panel is darkened. When the first LCD panel does not receive the AC control signals, the first LCD panel may be transparent.

When the second LCD panel receives the AC control signals, the light transmittance of the second LCD panel may be lowered, such that the second LCD panel is darkened. When the second LCD panel does not receive the AC control signals, the second LCD panel may be transparent.

In one embodiment of the power saving welding helmet, frequency of the AC control signals may be lower than 1 Hz. An area of the first LCD panel is greater than 85 square centimeters, and an area of the second LCD panel is greater than 85 square centimeters.

When a welder is not working, the welding arc is not active. The light sensor may not sense the welding arc to generate the light signals, and the filter control unit may not turn on the magnetic sensor. Therefore, the first LCD panel and the second LCD panel may not receive the control signals, and the first LCD panel and the second LCD panel may not be darkened. The welder does not have to take off the power saving welding helmet, and may still clearly see the surroundings through the filter lens.

When a welder is working, the welding arc is active. The light sensor may sense the welding arc to generate the light signals, and the control logic module may output the control signals. The first LCD panel and the second LCD panel may receive the control signals, and the first LCD panel and the second LCD panel may be darkened to protect eyes of the welder.

Further, the first LCD panel and the second LCD panel are controlled by the control signals. Therefore, the first LCD panel is controlled by the control signals with a phase shift and the second LCD panel is controlled by the control signals without the phase shift. Therefore, performances of the first LCD panel and the second LCD panel are complementary to each other. A refresh time of the first LCD panel and a refresh time of the second LCD panel do not synchronize. In the other words, when the first LCD panel is transparent, the second LCD panel is darkened, and vice versa. Therefore, the welder may not feel the first LCD panel or the second LCD panel flashing, and the welding experiences this as consistent darkness.

Since the lens device includes two LCD lenses controlled by different control signals, and the control signals of the first LCD panel and the control signals of the second LCD panel are not synchronized, frequency of the control signals may not be high enough to cause persistence of vision. The frequency of the control signals may be decreased. Therefore, power consumption caused by the control signals may also be decreased, and the power saving welding helmet may save more electric power.

Other objectives, advantages and novel features of the invention will become more apparent from the following detailed description when taken in conjunction with the accompanying drawings.

DETAILED DESCRIPTION OF THE INVENTION

Figure 1:
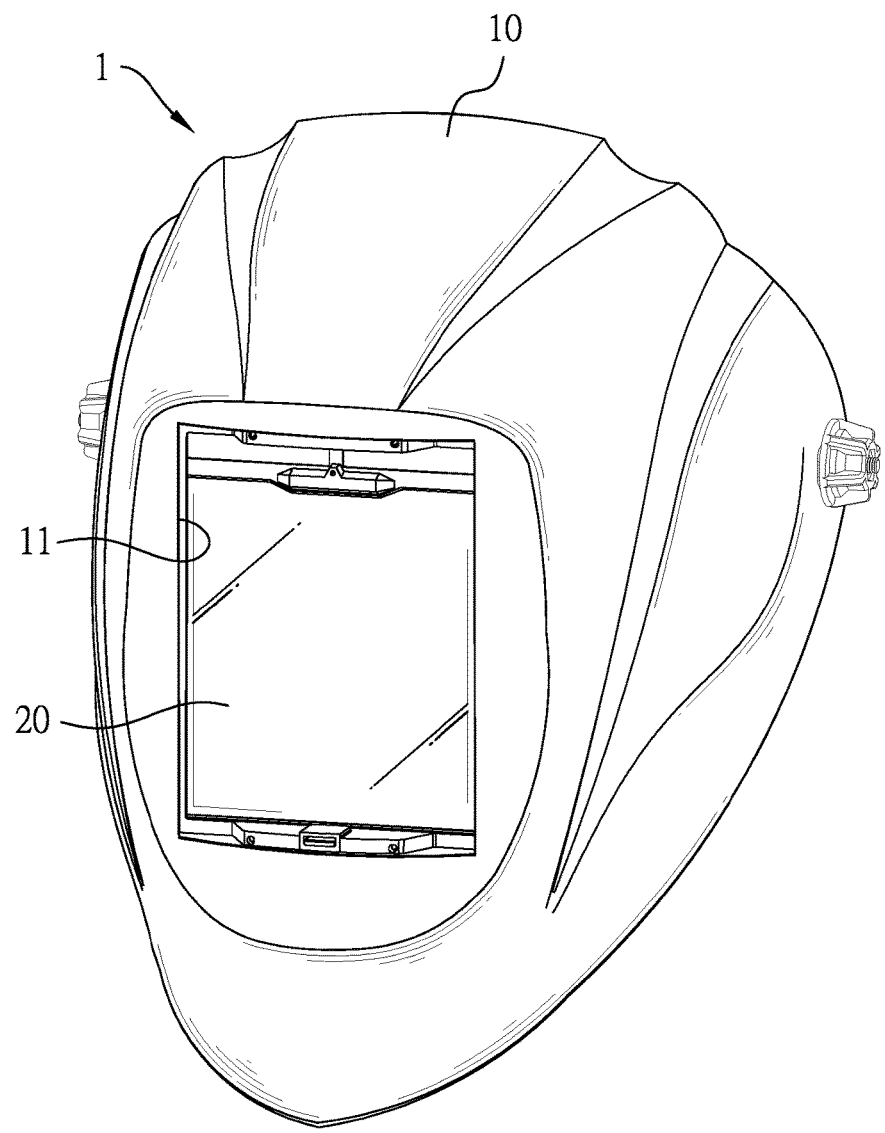
FIG. 1 is a schematic view of a power saving welding helmet of the present invention.

With reference to FIG. 1, the present disclosure is a power saving welding helmet 1. The power saving welding helmet 1 may reduce power consumption to save more electric power.

The power saving welding helmet 1 includes a helmet shell 10 and a lens device 20. The helmet shell 10 includes a mounting hole 11. The lens device 20 is mounted in the mounting hole 11 of the helmet shell 10.

Figure 2:
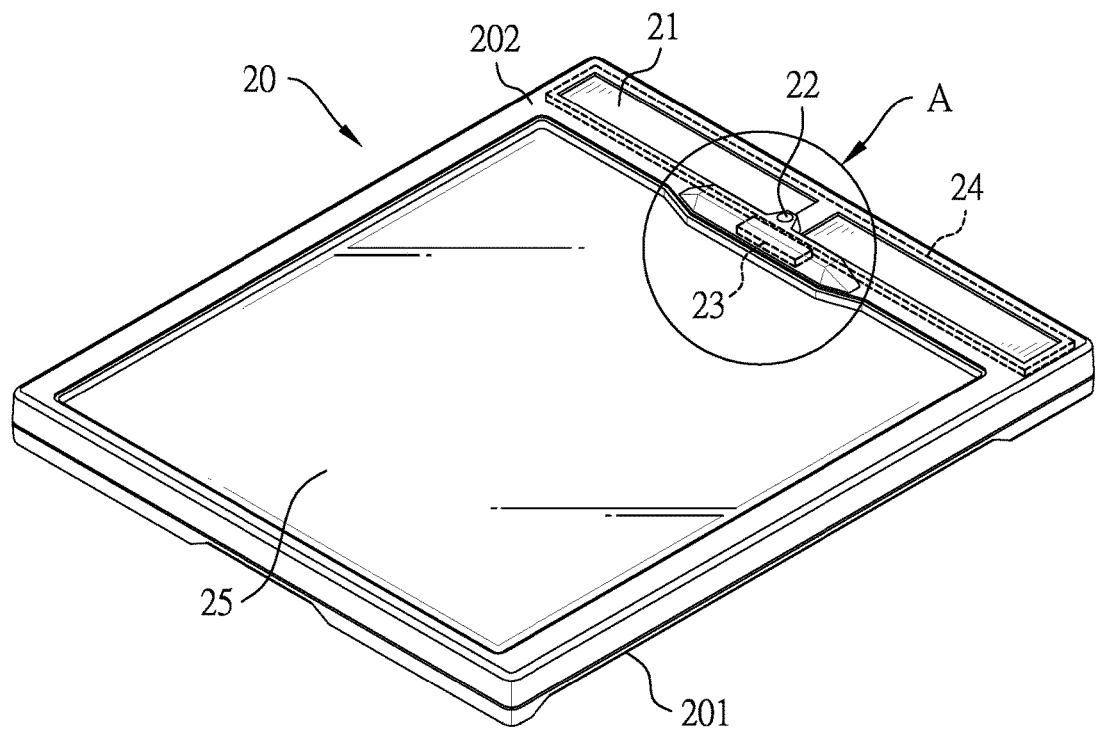
FIG. 2 is a schematic view of a lens device of the power saving welding helmet of FIG. 1.
Figure 3:
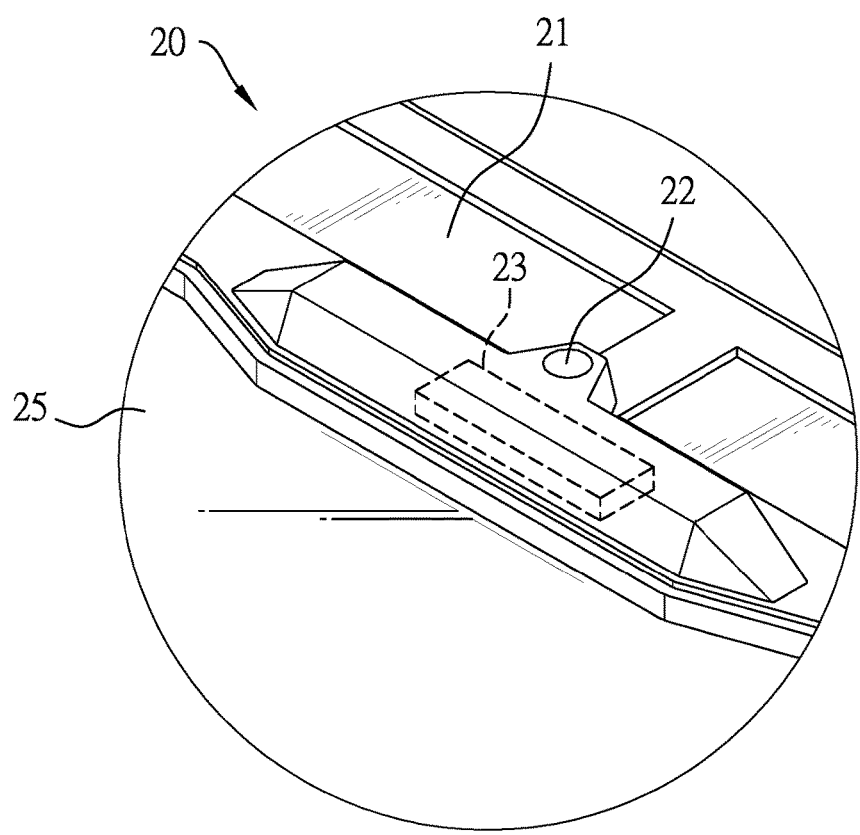
FIG. 3 is an enlarged view of the schematic diagram of the lens device of the power saving welding helmet of FIG. 2.

With reference to FIGS. 2 and 3, the lens device 20 has an inner surface 201 and an outer surface 202, and alternatively includes a solar panel 21, and a light sensor 22. The lens device 20 further includes a magnetic sensor 23, a filter control unit 24, and a filter lens 25.

Figure 5:
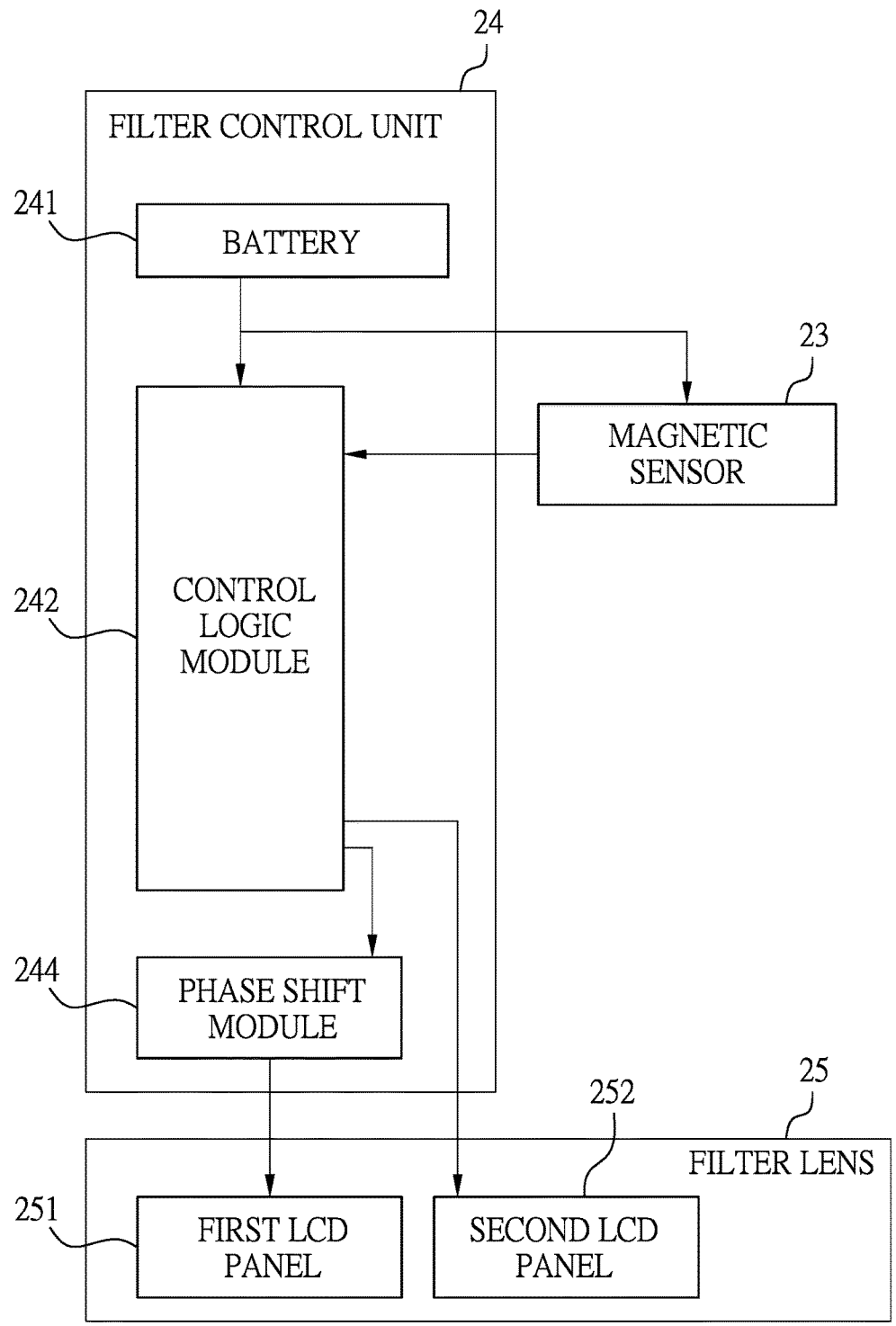
FIG. 5 is block diagram of the lens device of the power saving welding helmet of FIG. 1.

With reference to FIG. 5, in one embodiment, the lens device 20 may not include the solar panel 21, and the light sensor 22, but may include the magnetic sensor 23, the filter control unit 24, and the filter lens 25. The filter control unit 24 is electrically connected to the magnetic sensor 23, and the filter lens 25. The magnetic sensor 23 is mounted on the outer surface 202 of the lens device 20, and generates and transmits magnetic signals to the filter control unit 24.

The filter control unit 24 includes a battery 241, a control logic module 242, and a phase shift module 244. The battery 241 is electrically connected to and supplies the electric power to the control logic module 242, and the magnetic sensor 23.

The control logic module 242 receives the magnetic signals, and determines whether to generate and output control signals according to the magnetic signals.

The filter lens 25 is a viewing lens. The filter lens 25 includes a first liquid crystal display (LCD) panel 251 and a second LCD panel 252. The first LCD panel 251 is electrically connected to the control logic module 242 through the phase shift module 244 to receive the control signals shifted by the phase shift module 244. The second LCD panel 252 is directly electrically connected to the control logic module 242 to receive the control signals generated by the control logic module 242. The first LCD panel 251 and the second LCD panel 252 are stacked with each other.

When the first LCD panel 251 receives the control signals shifted by the phase shift module 244, the light transmittance of the first LCD panel 251 may be lowered, such that the first LCD panel 251 is darkened. When the first LCD panel 251 does not receive the control signals, the first LCD panel 251 may be transparent.

When the second LCD panel 252 receives the control signals, the light transmittance of the second LCD panel 252 may be lowered, such that the second LCD panel 252 is darkened. When the second LCD panel 252 does not receive the control signals, the second LCD panel 252 may be transparent.

In this embodiment, frequency of the control signals may be lower than 1 Hz. An area of the first LCD panel 251 is greater than 85 square centimeters, and an area of the second LCD panel 252 is greater than 85 square centimeters.

Figure 6:
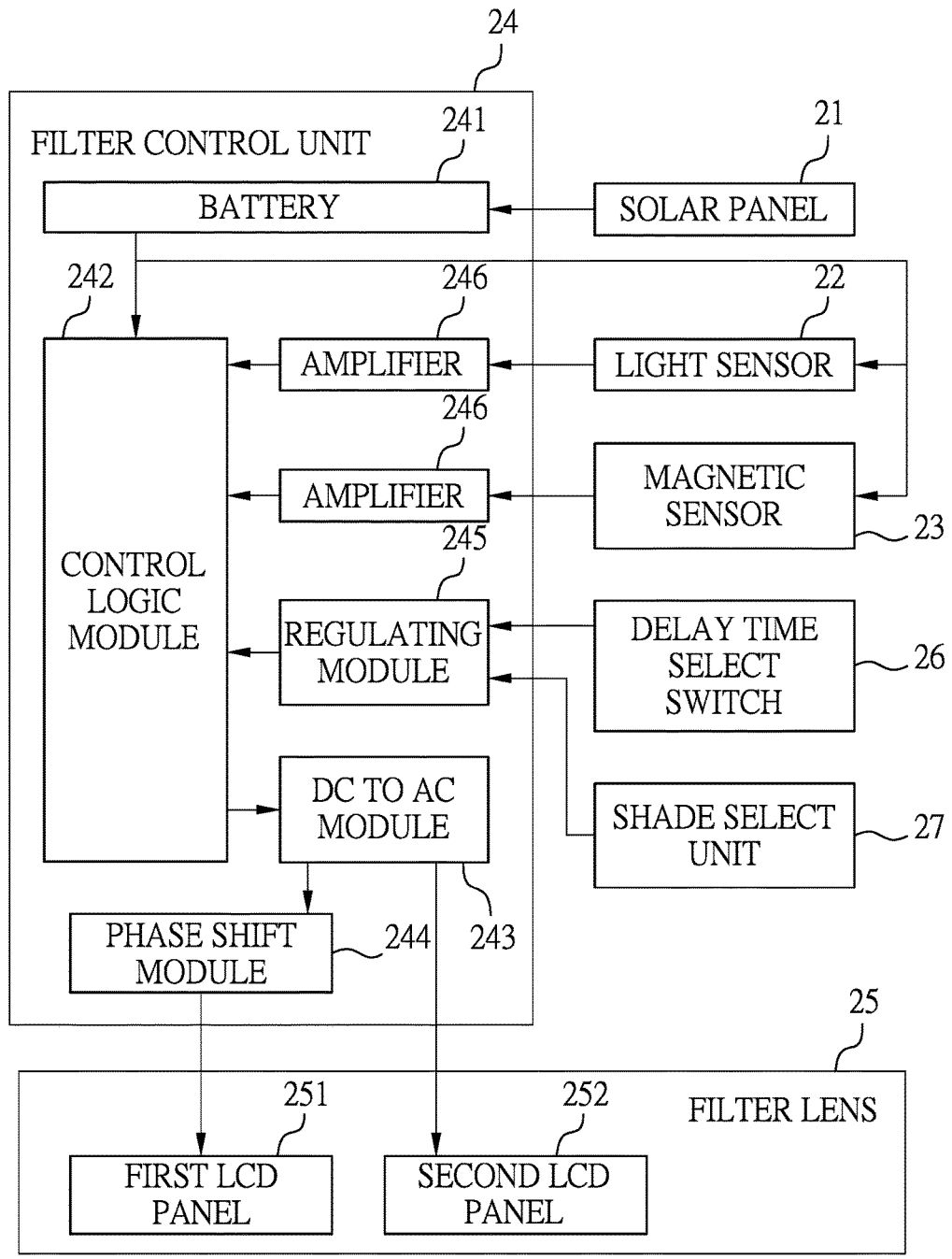
FIG. 6 is anther block diagram of the lens device of the power saving welding helmet of FIG. 1.
Figure 7:
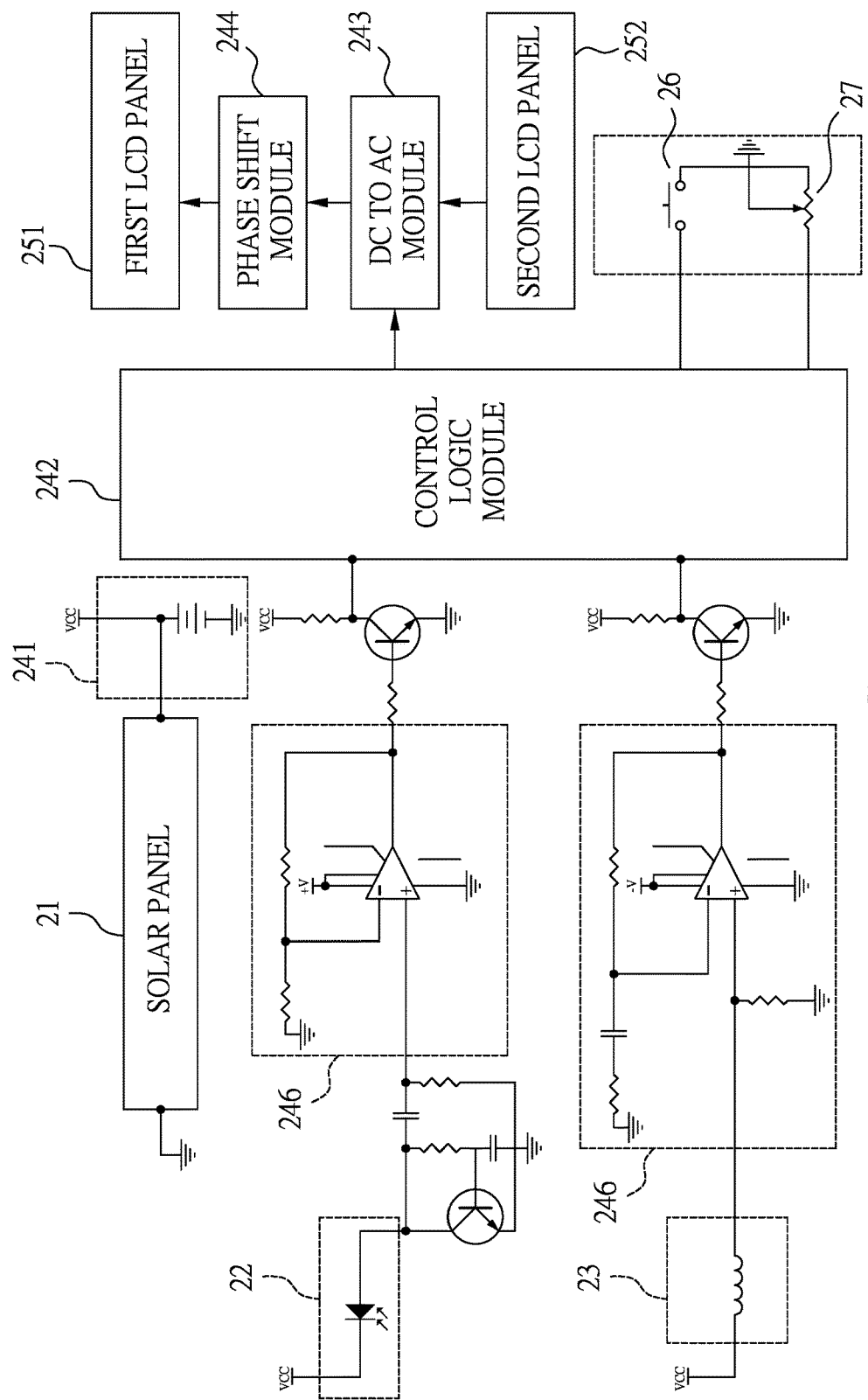
FIG. 7 is a circuit diagram of an embodiment for controlling the lens device of the power saving welding helmet of FIG. 1.

With reference to FIGS. 6 and 7, in another embodiment, the lens device 20 may include the solar panel 21, the light sensor 22, the magnetic sensor 23, the filter control unit 24, and the filter lens 25. The filter control unit 24 further includes a DC to AC module 243. The battery 241 is further electrically connected to the solar panel 21 to receive and store the electric power, and the battery 241 is electrically connected to and supplies the electric power to the light sensor 22. The solar panel 21 is mounted on the outer surface 202, generates electric power, and transmits the electric power to the filter control unit 24. The light sensor 22 is mounted on the outer surface 202 of the lens device 20, and senses ambient light to generate and transmit light signals to the filter control unit 24.

Figure 8:
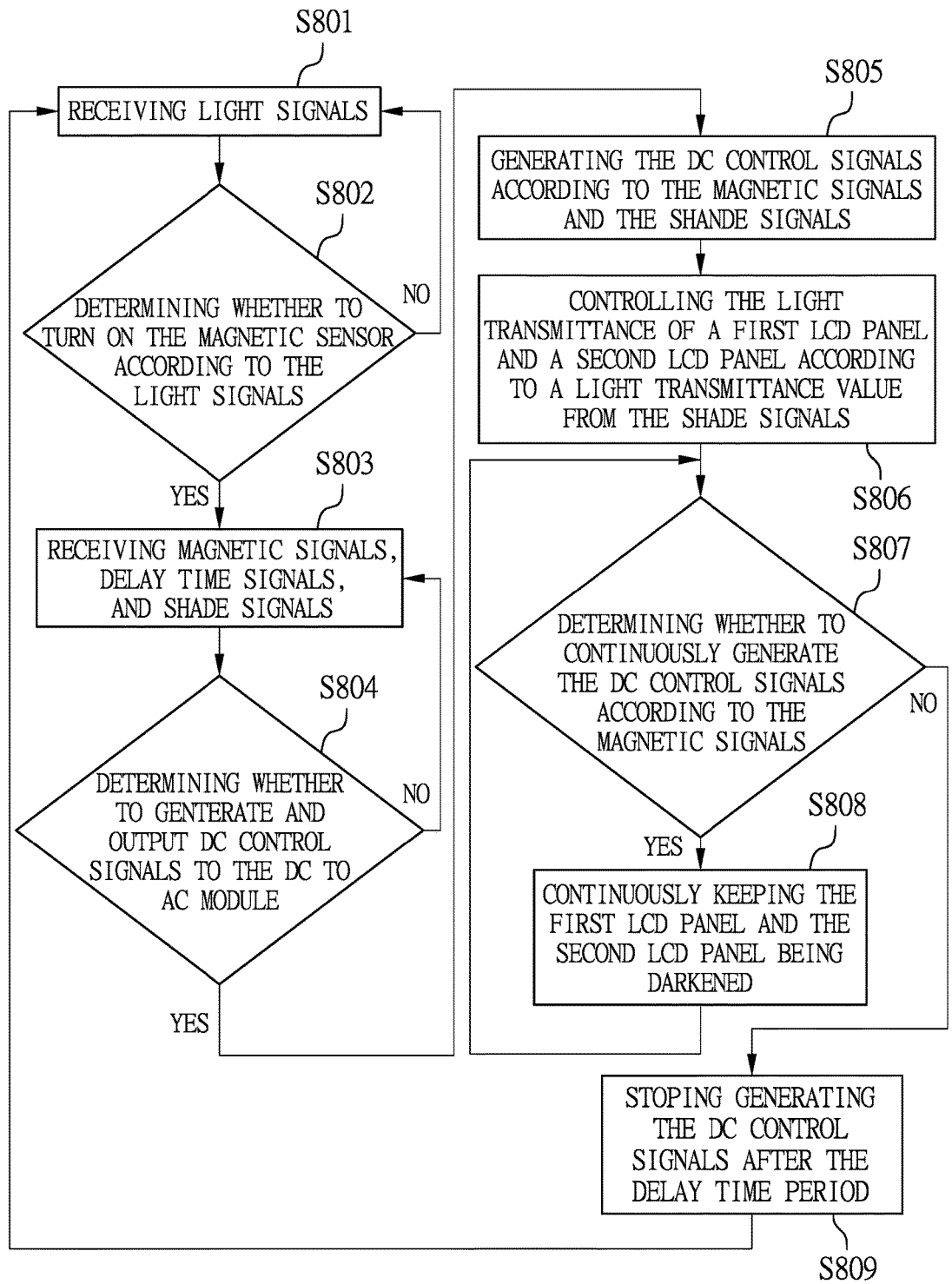
FIG. 8 is a flowchart of the lens device of the power saving welding helmet of an embodiment of the present invention.

As shown in FIG. 8, a flow chart of an embodiment is disclosed. In step S801, the control logic module 242 is electrically connected to the light sensor 22 to receive the light signals.

In step S802, when the control logic module 242 receives the light signals, the control logic module 242 determines whether to turn on the magnetic sensor 23 according to the light signals. In one embodiment, when the control logic module 242 determines signal strength of the light signals is greater than a light threshold, the control logic module 242 turns on the magnetic sensor 23.

In step S803, when the magnetic sensor 23 is turned on, the control logic module 242 receives the magnetic signals.

In step S804, the control logic module 242 determines whether to generate and output DC control signals to the DC to AC module 243 according to the magnetic signals.

In step S805, when the control logic module 242 generates and outputs the DC control signals to the DC to AC module 243, the DC to AC module 243 receives the DC control signals and generates AC control signals according to the DC control signals.

The filter lens 25 is a viewing lens. The filter lens 25 includes a first liquid crystal display (LCD) panel 251 and a second LCD panel 252. The first LCD panel 251 is electrically connected to the DC to AC module 243 through the phase shift module 244 to receive the AC control signals shifted by the phase shift module 244. The second LCD panel 252 is directly electrically connected to the DC to AC module 243 to receive the AC control signals generated by the DC to AC module 243. In one embodiment, the first LCD panel 251 and the second LCD panel 252 are stacked with each other.

In step S806, when the first LCD panel 251 receives the AC control signals shifted by the phase shift module 244, light transmittance of the first LCD panel 251 may be lowered, such that the first LCD panel 251 is darkened. When the second LCD panel 252 receives the AC control signals, light transmittance of the second LCD panel 252 may be lowered, such that the second LCD panel 252 is darkened.

Otherwise, when the first LCD panel 251 does not receive the AC control signals, the first LCD panel 251 may be transparent. When the second LCD panel 252 does not receive the AC control signals, the second LCD panel 252 may be transparent.

For example, when a welder is not working, the welding arc is not active. The light sensor 22 may not sense the welding arc to generate the light signals, and the filter control unit 24 may not turn on the magnetic sensor 23. Therefore, the first LCD panel 251 and the second LCD panel 252 may not receive the AC control signals, and the first LCD panel 251 and the second LCD panel 252 may not be darkened. The welder does not have to take off the power saving welding helmet and may still clearly see the surroundings through the filter lens 25.

When the welder is working, the welding arc is active. The light sensor 22 may sense the welding arc to generate the light signals, and the filter control unit 24 may turn on the magnetic sensor 23. When the magnetic sensor 23 is turned on, the control logic module 242 may generate and output the DC control signals to the DC to AC module 243. The DC to AC module 243 may generate the AC control signals. The first LCD panel 251 and the second LCD panel 252 may receive the AC control signals, and the first LCD panel 251 and the second LCD panel 252 may be darkened to protect eyes of the welder.

Further, the first LCD panel 251 and the second LCD panel 252 are controlled by the AC control signals respectively. Therefore, the first LCD panel 251 is controlled by the AC control signals with a phase shift and the second LCD panel 252 is controlled by the AC control signals without the phase shift. Therefore, performances of the first LCD panel 251 and the second LCD panel 252 are complementary to each other. A refresh time of the first LCD panel 251 and a refresh time of the second LCD panel 252 do not synchronize. In other words, when the first LCD panel 251 is transparent, the second LCD panel 252 is darkened, and vice versa. Therefore, the welder may not feel the first LCD panel 251 or the second LCD panel 252 flashing.

Since the lens device includes two LCD lenses controlled by different control signals, the control signals of the first LCD panel 251 and the control signals of the second LCD panel 252 are not synchronized, and frequency of the control signals may not be high enough to cause persistence of vision. The frequency of the control signals may be decreased. Therefore, power consumption caused by the control signals may also be decreased, and the power saving welding helmet may save more electric power.

Figure 4:
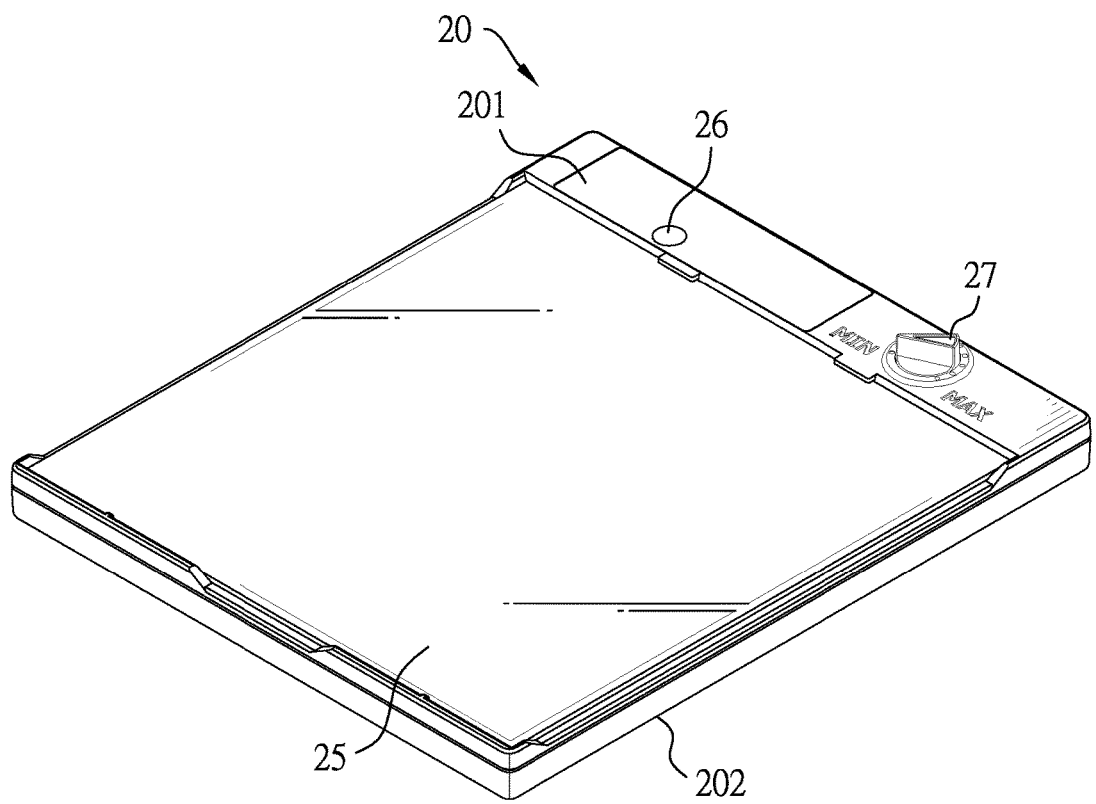
FIG. 4 is another schematic view of the lens device of the power saving welding helmet of FIG. 1.

With reference to FIGS. 4, 6, and 7, the filter control unit 24 further includes a regulating module 245. The lens device 20 further includes a delay time select switch 26 and a shade select unit 27. The delay time select switch 26 and the shade select unit 27 are mounted on the inner surface 201 of the lens device 20. The delay time select switch 26 and the shade select unit 27 are electrically connected to the filter control unit 24.

The delay time select switch 26 may generate and transmit delay time signals to the control logic module 242 through the regulating module 245. The shade select unit 27 may generate and transmit shade signals to the control logic module 242 through the regulating module 245.

The delay time signals may be adjusted by a user through operating the delay time select switch 26. The shade signals may be adjusted by the user through operating the shade select unit 27. In an embodiment, the delay time select switch 26 may be a button. The shade select unit 27 may be a potentiometer. The delay time signals may correspond to a delay time period.

In one embodiment, the light sensor 22 may be electrically connected to the control logic module 242 though an amplifier 246, and the magnetic sensor 23 may be electrically connected to the control logic module 242 through another amplifier 246.

As shown in FIG. 8, in step S803, when the magnetic sensor 23 is turned on, the control logic module 242 receives the magnetic signals, the delay time signals, and the shade signals, and further determines a light transmittance value of the first LCD panel 251 and the second LCD panel 252 according to the shade signals, and generates the DC control signals combined with the light transmittance value.

In step S804, when the control logic module 242 determines whether to generate and output DC control signals to the DC to AC module 243 according to the magnetic signals, the control logic module 242 may further receive the delay time signals and the shade signals.

In step S805, when the control logic module 242 determines to generate the DC control signals, the DC control signals may be generated according to the magnetic signals and the shade signals. Further, when the control logic module 242 generates and outputs the DC control signals to the DC to AC module 243, the DC to AC module 243 generates the AC control signals combined with the light transmittance value.

In step S806, the filter control unit 24 may control the light transmittance of the first LCD panel 251 and the second LCD panel 252 according to the light transmittance value from the shade signals. Namely, when the first LCD panel 251 receives the AC control signals shifted by the phase shift module 244, the first LCD panel 251 may be darkened according to the light transmittance value combined in the AC control signals. When the second LCD panel 252 receives the AC control signals, the second LCD panel 252 may be darkened according to the light transmittance value combined in the AC control signals.

In step S807, when the first LCD panel 251 and the second LCD panel 252 become dark, the control logic module 242 further determines whether to continuously generate the DC control signals according to the magnetic signals. In one embodiment, when the control logic module 242 determines signal strength of the magnetic signals is greater than a magnetic threshold, the control logic module 242 continuously generates the DC control signals.

In step S808, when the control logic module 242 determines to continuously generate the DC control signals according to the magnetic signals, the first LCD panel 251 and the second LCD panel 252 may continuously receive the AC control signals and keep darkened according to the light transmittance value.

In step S809, when the control logic module 242 determines not to continuously generate the DC control signals according to the magnetic signals, the control logic module 242 may keep generating the DC control signals, and may stop generating the DC control signals upon expiration of the delay time period corresponding to the delay time signals. Therefore, when the control logic module 242 determines not to continuously generate the DC control signals according to the magnetic signals, the first LCD panel 251 and the second LCD panel 252 may be transparent after the delay time period expires.

The delay time period may be a safeguard against flash burn, ultraviolet light, sparks, infrared light, and heat. When the welder just finishes welding, the first LCD panel 251 and the second LCD panel 252 may keep darkened during the delay time period to protect the eyes of the welder from damage.

Figure 9A:
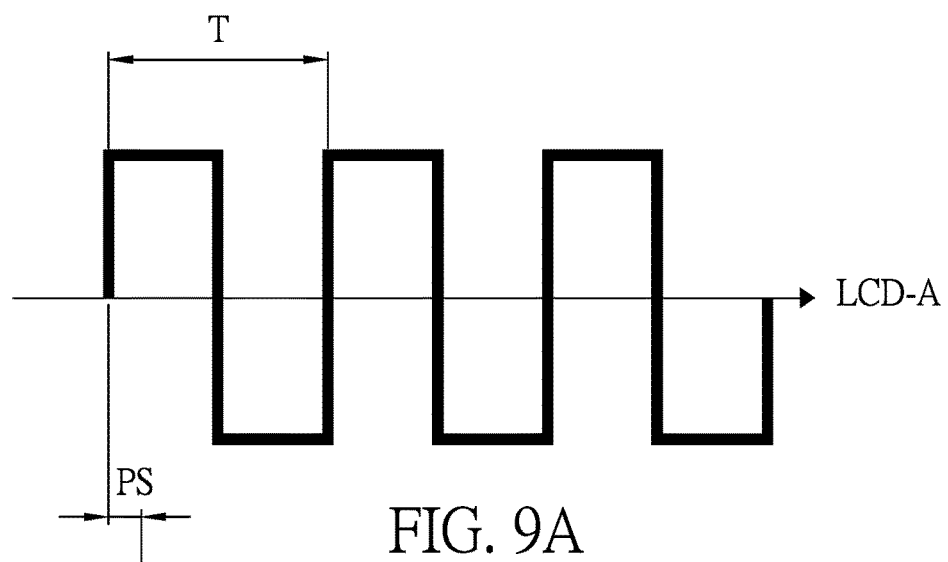
FIG. 9A and FIG. 9B are waveform diagrams of controlling signals of the lens device of the power saving welding helmet of FIG. 1.
Figure 9B:
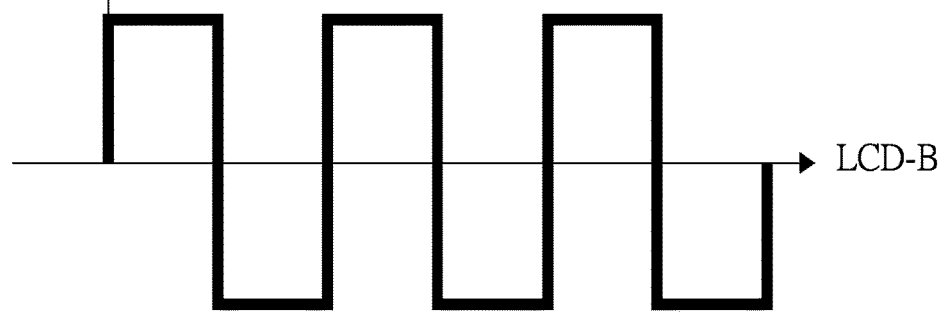

With reference to FIGS. 9A and 9B, in one embodiment of the present disclosure, the AC control signals may be square wave signals. The frequency of the AC control signals is smaller than 1 Hz. In other words, the period T of the AC control signals is greater than 1 second. Values of peaks of the square wave signals may correspond to the light transmittance value of the first LCD panel 251 and the second LCD panel 252. The first LCD panel 251 is controlled by AC control signals LCD-A, the second LCD panel 252 is controlled by AC control signals LCD-B, and the AC control signals LCD-A may have a phase shift PS with the AC control signals LCD-B.

Since the first LCD panel 251 is controlled by the AC control signals with the phase shift and the second LCD panel 252 is controlled by the AC control signals without the phase shift, the refresh time of the first LCD panel 251 and the refresh time of the second LCD panel 252 may not synchronize. Therefore, when the frequency of the AC control signals is lower than 1 Hz, the welder may not feel the first LCD panel 251 or the second LCD panel 252 fleshing.

In FIG. 9A, the AC control signals LCD-B without the phase shift PS may be outputted to the first LCD panel 251. In FIG. 9B, the AC control signals LCD-A with the phase shift PS may be outputted to the second LCD panel 252.

Figure 10:
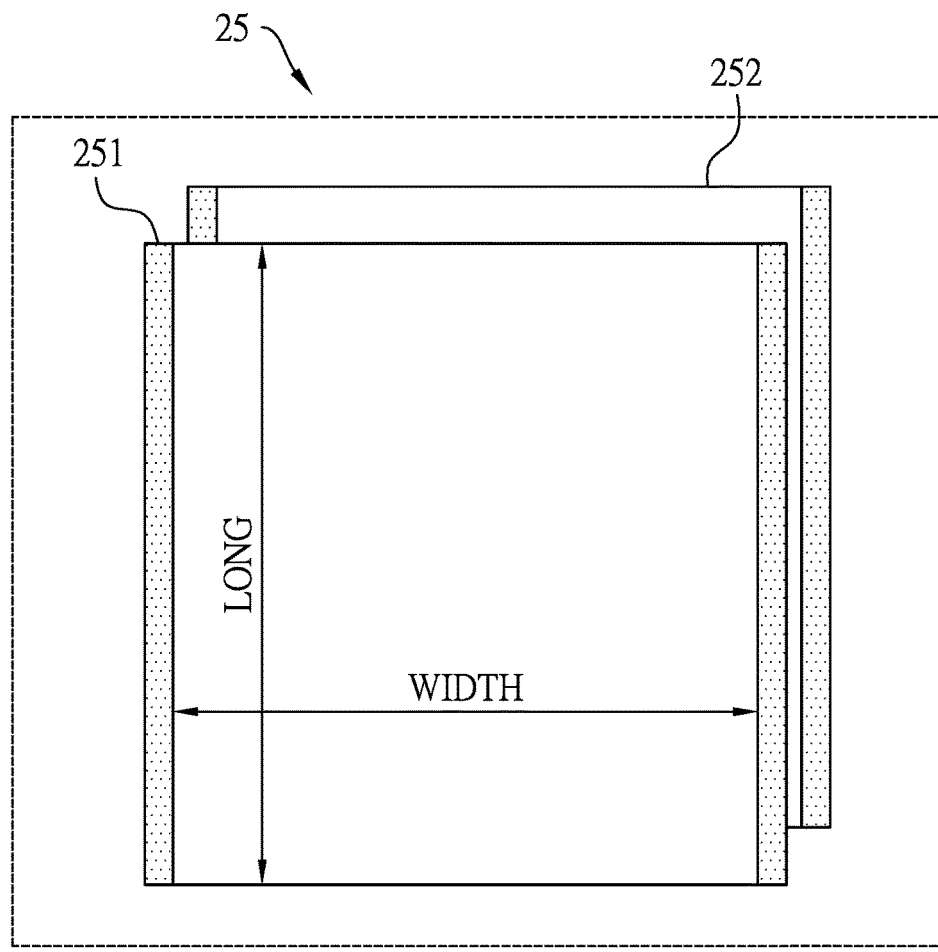
FIG. 10 is a schematic view of a first LCD panel and a second LCD panel of the lens device of the power saving welding helmet of FIG. 1.

With reference to FIG. 10, an area of the first LCD panel 251 may be calculated by multiplying a length of the first LCD panel 251 with a width of the first LCD panel 251. An area of the second LCD panel 252 may be calculated by multiplying a length value of the second LCD panel 252 with a width value of the second LCD panel 252. In the embodiment, the first LCD panel 251 and the second LCD panel 252 may be integrated into one component.

In one embodiment of the present disclosure, the area of the first LCD panel 251 may be greater than 85 square centimeters, and the area of the second LCD panel 252 may be greater than 85 square centimeters.

Since the frequency of the AC control signals may be lower than 1 Hz, the power consumption caused by the AC control signals may be decreased. In the premise of the same battery capacity, the filter control unit 24 may have enough electric power to drive the filter lens 25 of a large size.

Even though numerous characteristics and advantages of the present invention have been set forth in the foregoing description, together with details of the structure and function of the invention, the disclosure is illustrative only. Changes may be made in detail, especially in matters of shape, size, and arrangement of parts within the principles of the invention to the full extent indicated by the broad general meaning of the terms in which the appended claims are expressed.

What is claimed is:

1. A power saving welding helmet, comprising:
   a helmet shell, comprising a mounting hole; and
   a lens device, mounted in the mounting hole of the helmet shell; wherein the lens device comprises:
      an inner surface;
      an outer surface;
      a magnetic sensor, mounted on the outer surface, and generating magnetic signals;
      a filter control unit, electrically connected to the magnetic sensor to receive the magnetic signals;
      wherein the filter control unit comprises:
         a control logic module, electrically connected to the magnetic sensor to receive the magnetic signals; wherein
            the control logic module determines whether to generate and output control signals according to the magnetic signals;
         a phase shift module, electrically connected to the control logic module; and
         a battery, electrically connected to and supplying the electric power to the control logic module, and the magnetic sensor;
      a filter lens, being a viewing lens, and comprising:
         a first liquid crystal display (LCD) panel, electrically connected to the control logic module through the phase shift module to receive the control signals shifted by the phase shift module; and
         a second LCD panel, stacked with the first LCD panel, and directly electrically connected to the control logic module to receive the control signals generated by the control logic module;
      wherein when the first LCD panel receives the control signals shifted by the phase shift module, light transmittance of the first LCD panel is lowered;
      wherein when the second LCD panel receives the control signals, light transmittance of the second LCD panel is lowered;
      wherein when the first LCD panel does not receive the control signals shifted by the phase shift module, the first LCD panel is transparent;
      wherein when the second LCD panel does not receive the control signals, the second LCD panel is transparent.

2. The power saving welding helmet as claimed in claim 1, wherein a frequency of the control signals is lower than 1 Hz.

3. The power saving welding helmet as claimed in claim 1, wherein:
   an area of the first LCD panel is greater than 85 square centimeters;
   an area of the second LCD panel is greater than 85 square centimeters.

4. The power saving welding helmet as claimed in claim 1, wherein the control signals are square wave signals.

5. The power saving welding helmet as claimed in claim 1, wherein the first LCD panel and the second LCD panel are integrated into one component.

6. The power saving welding helmet as claimed in claim 5, wherein:
   when the magnetic sensor is turned on, the control logic module further determines a light transmittance value of the first LCD panel and the second LCD panel according to the shade signals, and generates the DC control signals combined with the light transmittance value;
   when the control logic module determines whether to generate and output the DC control signals to the DC to AC module according to the magnetic signals, the control logic module further receives the delay time signals and the shade signals;

when the control logic module determines to generate the DC control signals, the DC control signals are generated according to the magnetic signals and the shade signals;

when the control logic module generates and outputs the DC control signals to the DC to AC module, the DC to AC module generates the AC control signals combined with the light transmittance value;

the filter control unit controls the light transmittance of the first LCD panel and the light transmittance of the second LCD panel according to the light transmittance value from the shade signals;

when the first LCD panel and the second LCD panel become dark, the control logic module further determines whether to continuously generate the DC control signals according to the magnetic signals;

when the control logic module determines to continuously generate the DC control signals according to the magnetic signals, the first LCD panel and the second LCD panel continuously receive the AC control signals and keep darkened according to the light transmittance value;

when the control logic module determines not to continuously generate the DC control signals according to the magnetic signals, the control logic module keeps generating the DC control signals, and stops generating the DC control signals upon expiration of the delay time corresponding to the delay time signals.

7. The power saving welding helmet as claimed in claim 6, wherein when the control logic module determines signal strength of the magnetic signals is greater than a magnetic threshold, the control logic module continuously generates the DC control signals.

8. The power saving welding helmet as claimed in claim 1, wherein the lens device further comprises:
 a solar panel, mounted on the outer surface, and generating electric power;
 a light sensor, mounted on the outer surface, and generating light signals;
 wherein the battery is electrically connected to the solar panel to receive and store the electric power, and further electrically connected to and supplying the electric power to the light sensor;
 wherein the filter control unit is further electrically connected to the solar panel, and the light sensor to receive the electric power, and the light signals;
 wherein the control logic module is further electrically connected to the light sensor;
 wherein when the control logic module receives the light signals, the control logic module determines whether to turn on the magnetic sensor according to the light signals; and
 wherein when the magnetic sensor is turned on, the control logic module receives the magnetic signals;
 wherein the control signals generated by the control logic module are DC control signals;
 wherein the filter control unit further comprises:
  a DC to AC module, electrically connected to the control logic module to receive the DC control signals; wherein the control logic module is electrically connected to the phase shift module through the DC to AC module, and is electrically connected to the first LCD panel through the DC to AC module;
  wherein when the DC to AC module receives the DC control signals, the DC to AC module generates AC control signals according to the DC control signals;
 wherein the first LCD panel is electrically connected to the DC to AC module through the phase shift module to receive the AC control signals shifted by the phase shift module;
 wherein the second LCD panel is electrically connected to the DC to AC module to receive the AC control signals generated by the DC to AC module.

9. The power saving welding helmet as claimed in claim 8, wherein:
 the light sensor senses ambient light to generate and transmit light signals to the filter control unit;
 when the control logic module determines signal strength of the light signals is greater than a light threshold, the control logic module determines to turn on the magnetic sensor.

10. The power saving welding helmet as claimed in claim 8, wherein the filter control unit further comprises a regulating module;
 wherein the lens device further comprises:
  a delay time select switch, mounted on the inner surface of the lens device, and electrically connected to the filter control unit; wherein the delay time select switch generates and transmits delay time signals to the control logic module through the regulating module; and
  a shade select unit, mounted on the inner surface of the lens device, and electrically connected to the filter control unit; wherein the shade select unit generates and transmits shade signals to the control logic module through the regulating module.

11. The power saving welding helmet as claimed in claim 10, wherein the delay time select switch is a button.

12. The power saving welding helmet as claimed in claim 10, wherein the shade select unit is a potentiometer.

\* \* \* \* \*